United States Patent
Cohade et al.

(10) Patent No.: US 11,938,003 B2
(45) Date of Patent: Mar. 26, 2024

(54) OPTIMIZED SUPPORT BANDAGE

(71) Applicant: URGO RECHERCHE INNOVATION ET DEVELOPPEMENT, Chenove (FR)

(72) Inventors: Céline Cohade, Saint-Jean-Bonnefonds (FR); David Grange, Bellegarde en Forez (FR); Magali Roblot, Perrigny-les-Dijon (FR); Serge Lecomte, Dijon (FR)

(73) Assignee: URGO RECHERCHE INNOVATION DEVELOPPEMENT, Chenove (FR)

( * ) Notice: Subject to any disclaimer, the term of this patent is extended or adjusted under 35 U.S.C. 154(b) by 417 days.

(21) Appl. No.: 16/613,327

(22) PCT Filed: May 17, 2018

(86) PCT No.: PCT/FR2018/051191
§ 371 (c)(1),
(2) Date: Nov. 13, 2019

(87) PCT Pub. No.: WO2018/211223
PCT Pub. Date: Nov. 22, 2018

(65) Prior Publication Data
US 2021/0077305 A1  Mar. 18, 2021

(30) Foreign Application Priority Data
May 19, 2017  (FR) ........................ 1754479

(51) Int. Cl.
*A61F 13/08* (2006.01)
*D04B 21/18* (2006.01)
(52) U.S. Cl.
CPC .............. *A61F 13/08* (2013.01); *D04B 21/18* (2013.01); *D10B 2403/0213* (2013.01); *D10B 2509/028* (2013.01)

(58) Field of Classification Search
CPC .... A61F 13/08; A61F 13/00; A61F 13/00008; A61F 13/00021; A61F 2013/00089;
(Continued)

(56) References Cited

U.S. PATENT DOCUMENTS 5,385,036 A   1/1995  Spillane et al.
6,755,052 B1 * 6/2004  Sytz ........................ D04B 1/18
                                                        66/196
(Continued)

FOREIGN PATENT DOCUMENTS

CN   102525737 A   7/2012
CN   103343421 A   10/2013
(Continued)

OTHER PUBLICATIONS

Dhingra et al (Shear Properties of Warp-Knitted Outerwear Fabrics; Textile Research Journal; pp. 526-529; Sep. 1979) (Year: 1979).*
(Continued)

*Primary Examiner* — Caitlin A Carreiro
(74) *Attorney, Agent, or Firm* — Lippes Mathias LLP

(57) ABSTRACT

A compression bandage in the form of a knit obtained with warp knit technology, formed of synthetic yarns and composed of two textile surfaces having the same or different textile structure, linked together by spacer threads, each surface has elastic yarns, and the spacer threads of the knit are multifilaments. The knit has longitudinal elongation measured as per standard EN 14704-1 of between 30 and 160% and threshold shear stress equal to or higher than 2800 Pa and/or conformability equal to or lower than 65 mm.

15 Claims, 4 Drawing Sheets

(58) Field of Classification Search
CPC .. A61F 2013/00238; A61F 2013/00119; A61F 2013/00361; B32B 5/026; D04B 11/12; D04B 7/16; D04B 7/30; D04B 1/22; D04B 1/18; D04B 1/265; D04B 21/18; D04B 21/16; D04B 21/20; D04B 21/00; D04B 23/06; D10B 2403/0213; D10B 2403/023; D10B 2509/028; D10B 2509/02; D10B 2509/022
USPC .... 602/41–44, 53, 62, 75–76; 428/190, 193, 428/197; 66/170, 172 E; 442/304, 306, 442/312, 318
See application file for complete search history.

(56) References Cited

U.S. PATENT DOCUMENTS

| | | | |
|---|---|---|---|
| 2002/0099318 A1* | 7/2002 | Suehr | A61F 13/08 602/76 |
| 2006/0156451 A1* | 7/2006 | Klein | A41D 31/102 2/159 |
| 2010/0305535 A1* | 12/2010 | Leeming | A61F 13/069 602/44 |

FOREIGN PATENT DOCUMENTS

| | | | | |
|---|---|---|---|---|
| CN | 103857414 A | 6/2014 | | |
| CN | 105431116 A | 3/2016 | | |
| EP | 1 052 3419 A1 | 11/2000 | | |
| GB | 2473321 A | 3/2011 | | |
| WO | WO 95/16416 | 6/1995 | | |
| WO | WO-9516416 A1 * | 6/1995 | ....... | A61F 13/00008 |
| WO | WO 2007/113430 A1 | 10/2007 | | |
| WO | WO 2009/071894 A1 | 6/2009 | | |

OTHER PUBLICATIONS

Arumugam et al (In-plane Shear Behavior of 3D Spacer Knitted Fabrics; Journal of Industrial Textiles; 2016, vol. 46(3) 868-886) (Year: 2016).*

Chinese Search Report of Related CN 201880046880.2 dated Dec. 14, 2020, 2 pages.

International Search Report for PCT/FR2018/051191, Authorized Officer Dieter Sterle, Date of Actual Completion Sep. 12, 2018, 2 pages.

* cited by examiner

OPTIMIZED SUPPORT BANDAGE

BACKGROUND OF THE DISCLOSURE

The present disclosure relates to an optimized compression bandage having longitudinal elongation of between 30% and 160%, being a 3D knit with multifilament spacer yarn obtained with "warp-knit" technology, without latex or adhesive, which does not slacken and thereby allows maintained therapeutic efficacy and prevents slippage over time

STATE OF ART

The use of various compression systems is known for the treatment of pathologies of venous origin e.g. venous insufficiency, the treatment of varicose veins and leg ulcers, or to prevent venous thrombosis or to treat lymphedema. These systems are composed of one or more bandages which apply pressure to the limb to be treated.

To be efficient, this system must allow the simultaneous application of:
first, relatively low pressure called "resting pressure" when the muscle is relaxed, to obtain conformability and in particular tolerability at night; and
secondly relatively high pressure called "working pressure", when the muscle is contracted or for movement especially when walking.

This pressure difference between working pressure and resting pressure must be sufficient to promote venous return. It is generally considered that a pressure difference at 24 hours of between 15 and 25 mm of mercury is required to restore correct blood flow. However, depending on pathology, whether for treatment of non-serious leg ulcers, difficult treatment of oedema-damaged legs, or the treatment of a mixed arterial and venous ulcer, this range of values can extend from 10 to 35 mm of mercury even from 10 to 40 mm of mercury.

The compression bandages in use are classified by compression specialists into two major categories according to their measured elongation: so-called short-stretch bandages and so-called long-stretch bandages.

This classification is based on measurement of the longitudinal elongation of the bandage such as defined in method A § 9.1 of standard EN 14704-1 when the bandage is subjected to a maximum tensile force of 6 N/cm.

The conditions for conducting this measurement are the following: A test specimen of material 50 mm in width and 250 to 300 mm in length is cut and positioned nor-prestressed in the jaws of an electronic dynamometer (e.g. a dynamometer of MTS trademark) so as to obtain an effective reference width of 50 mm and length of 200 mm. The dynamometer stretches the test specimen at a rate of 100 mm/min until a maximum force of 6 N/cm is reached, after which the cross-member returns to its initial position at the same rate of return of 100 mm/min. This cycle is repeated 5 times and the elongation obtained at the fifth cycle, expressed as a percentage, is directly calculated by the apparatus. The operation is repeated on 5 test specimens and the mean value is calculated which defines the longitudinal elongation of the bandage.

The transverse elongation of the bandage can be evaluated following the same protocol.

Short-Stretch Bandages

On this basis of this test in accordance with standard EN 14704-1 taken as reference, it is considered that a compression bandage is "short-stretch" if its longitudinal elongation is equal to or less than 100%. These bandages apply a low resting pressure and high working pressure.

They therefore have a large pressure difference in particular during movement e.g. when walking.

Long-Stretch Bandages

On the basis of the preceding test in accordance with standard EN 14704-1 taken as reference, it is considered that a bandage is "long stretch" if its longitudinal elongation higher than 100%.

These bandages are easier to apply since they have greater extensibility.

Long-stretch bandages lead to low variations between resting and working pressure, and to a small variation in pressure during movement e.g. when walking. They prove to be less efficient than short-stretch bandages. On the other hand, on account of this low difference in pressure they are subjected to smaller stress forces than short-stretch bandages and therefore carry a lesser risk of slackening and hence of slippage on the leg than short-stretch bandages.

It is currently known that the best performing compression systems in terms of quick and easy application and in terms of therapeutic efficacy are those which comprise no more than 2 bandages and at least one so-called short-stretch compression bandage.

For example, mention can be made of the products marketed under the trade names ACTICO, K2 and Coban 2 marketed by ACTIVA, URGO and 3M respectively.

The ACTICO system is composed of one self-adhering short-stretch bandage wound around a strip of wadding previously wound around the leg. The wadding is intended to distribute pressures over the surface of the limb and/or to protect bony prominences via its thickness, and to absorb any exudates if the bandage is applied onto an open wound e.g. In the event of leg ulcers.

The K2® system marketed by URGO is composed of a first bandage (marketed under the trade name Ktech®) which is a short-stretch bandage formed of a layer of wadding in contact with the skin and needled to an elastic knit, and of a second elastic, self-adhering bandage (marketed under the trade name KPress®) which is a long-stretch bandage used to maintain the first bandage in place and to apply additional pressure to that of the first bandage so that the desired pressure can be obtained.

The Coban system is composed of a first bandage applied without stretching and formed of a foam in contact with the skin in association with a self-adhering bandage, and of a second self-adhering bandage which is a short-stretch bandage intended to apply the desired pressure and to maintain the system in place.

One disadvantage of these different systems is that, to guarantee their maintained positioning and efficacy, the self-adhesion of the bandages is obtained with the aid of adhesive or latex which complicates their design and can lead to risks of allergy in contact with the skin, the case in particular with natural rubber latex.

However, the presence of the adhesive or latex is inescapable since it has the role of maintaining the bandage or system in place after it has been wound around the limb, and of reducing intrinsic slackening which would lead to loss of efficacy and slippage along the limb.

On the other hand, incorporation of an adhesive or latex makes production more complex since it modifies the pressure and pressure difference properties of the bandage onto which they are applied.

To improve patient and nursing staff acceptability and to obtain a product that is easier to produce, it therefore appears desirable to provide a compression system which uses adhesive-free and latex-free bandages.

So-called 3D-knits are products in the form of 2 independent textile surfaces (knits) linked together by spacer threads, hence their name "3D". Said products are used for example in the field of motor vehicle seats for their compressive capacity. To obtain this capacity however these knits are thick, rigid and highly elastic. They are similarly used in the textile industry for brassiere cup parts. These knits are very soft to the touch but again highly elastic to ensure support. In both cases, they are not adapted to meet the properties of a compression bandage.

Other 3D knits adapted for compression were proposed in patent application WO 95/16416.

The problem that this application WO 95/16416 set out to solve was to eliminate the wadding. Over time, wadding collapses leaving a clearance between the leg and the bandage during movements which can cause the assembly to slip. The objective was to compensate for this collapsing phenomenon by means of the 3D structure and thickness of the knit to obtain a good cushioning effect and eliminate the need for wadding. To obtain this result, the described 3D knits have high gram weights and thickness. This leads to producing compression bandages that are bulkier and hence less easy to handle since they are in the form of thicker rolls. They are also heavier, increasing the risk of easier slippage over time.

It was to overcome this shortcoming and the absence of latex or adhesive that document WO 2009/71894 proposed incorporating an adhesive or latex in the 3D knits proposed in document WO 95/16416, which also raises the aforementioned problems with respect to adhesive or latex in terms of production and allergy risks.

Patent application GB 2473321 proposes the obtaining of 3D knits again with high gram weights to approximate the cushioning role of the wadding whilst applying pressures and pressure differences adapted to the therapeutic objectives. However, all the described knits produced use "weft knit" technology. From an industrial production viewpoint, this technology is not adapted for the manufacture of a compression bandage since a sheet of 3D knit when cut leads to unravelling of the product. The problem of slippage over time is also raised for products obtained in conformity with the teaching of this document.

To overcome this problem, document GB 2473321 proposes making 3D knits cohesive by adding silica derivatives alone or in association with latex or acrylates to ensure maintained positioning over time (such as mentioned on page 14 of this document), which also raises the aforementioned problems in terms of production and allergy risks.

The slippage of a bandage is caused by 3 major factors.

The first factor is related to the quality of application. If a bandage is applied with too little stretch it risks slipping since the pressure applied to the limb is insufficient to hold the bandage in place. A calibration device can solve this problem and also prevent the reverse problem of a bandage that is stretched too much which will apply pressure that is too high and could lead to forming a tourniquet. Similarly, it is necessary for the last spiral to be securely fastened so that it does not become slack at its end portion and subsequently over the entire winding thereof which will lead to loss of therapeutic efficacy and even slippage along the leg. Various devices are used to reinforce this fastening.

The second factor is related to the bandage's capacity to resist slippage on the skin, which is dependent upon the surface condition in contact with the skin. This aspect is difficult to offset since it is desirable to have a surface in contact with the skin that is the least unpleasant to the touch as possible to promote patient compliance for wearing the bandage.

The third factor is related to the operating mode of the bandage. A balance must be found between the force applied by the extended bandage during variations in calf diameter, and its capacity to prevent lateral spiral-over-spiral slippage evidencing intrinsic slackening and translating the fact that it has loosened after application. The same phenomenon then occurs as with deficient application i.e. loss of therapeutic efficacy and even, in the event of transmission of this lateral spiral-over-spiral slippage of the bandage over time, to vertical sliding of the bandage which can lead to the bandage falling off. This phenomenon is amplified by the weight of the bandage.

This third factor, the cause of slippage, is particularly important and is also the main reason for the loss of efficacy of compression systems over time.

Paradoxically, this cause of slippage has not been studied in depth up until now. To solve this problem, and to oppose this intrinsic slackening, the bandages have been made "cohesive", i.e. priority given to incorporating latex or adhesive in compression bandages. Therefore, in all short-stretch bandage compression systems in which this phenomenon is the greatest, at least one cohesive bandage is currently incorporated which again raises the problems defined above.

In the absence of cohesiveness or any other means to avoid this phenomenon of slippage, if the 2 first factors are mastered the third factor then becomes essential. Therapeutic efficacy and intrinsic slackening of the bandage increasing the possibility of slippage are closely linked to this balance and how it develops over time.

To conclude, although the use of a 3D knit as compression bandage has been proposed for nearly 20 years now, no solution appears to be fully satisfactory to obtain a 3D knit which has short-stretch behaviour allowing the right pressure difference to be obtained and which, in the absence of latex or adhesive, allows maintained positioning thereof and prevents the risk of slippage on the limb over time.

Accordingly, there exists a need for an optimized support bandage that overcomes the above-mentioned difficulties and others, while providing better overall results.

SUMMARY OF THE DISCLOSURE

To solve these highly complex specifications having contradictory properties, the present disclosure has examined the friction forces applied to a self-contacting bandage under the effect of pressure corresponding to desired therapeutic treatment pressure e.g. for a leg ulcer of approximately 35 to 50 mm of mercury. Slippage of the spirals of a bandage is related to micromovements within the bandage imposed by the weight thereof under gravity and to repetitive friction forces induced by variations in calf diameter during movements.

To conduct hitherto never envisaged measurement of these micromovements within the bandage, which are very small, the present disclosure used rheometer apparatus conventionally used to measure the rheological properties of soft materials. In addition to allowing determination of very small forces, this apparatus can also apply shear torque i.e. torsion to represent friction stresses applied to the bandage both in the longitudinal direction and transverse direction thereof. The technique developed allowed determination of the minimum shear force responsible for the first micromovement undergone by the bandage wound around itself and which will lead to lateral slippage of the spirals and slackening of the bandage. This shear force is called the threshold shear stress since it measures the first micromovement and is expressed in Pascal.

This measurement gave better understanding of the phenomena involved and determined the essential characteristics that a 3D knit should have to meet the above-listed properties and in particular the threshold shear stress required to prevent intrinsic slackening of the bandage so that it can maintain its therapeutic efficacy and remain non-slip.

Therefore, a 3D knit in which the spacer thread is a monofilament having a threshold shear stress equal to or higher than 2800 Pa can ensure non-slippage of spiral over spiral in the compression bandage.

The present disclosure was notably able to ascertain that in a 3D knit the spacer thread separating and linking the two textile surfaces plays a major role.

The present disclosure was particularly able to ascertain that the rigidity of the spacer thread impacts the spacing between the two textile surfaces at rest and during deformation of the structure of the 3D knit when the latter is subjected to the stretching stresses of a compression bandage.

Yet a compression bandage must be both flexible and comfortable, the least thick possible, but it must also have some rigidity in extension.

To obtain a product able to correspond to these complex specifications having antagonistic properties, and to optimize flexibility without affecting the other properties, the present disclosure has examined the use of multifilament yarns as spacer thread.

To assess the impact of said multifilament yarns, the present disclosure examined their rigidity. To do so, the present disclosure used a model in which the thread is considered to be the equivalent of a homogeneous beam with circular cross-section.

On the basis of this model, the thread's second moment of area was calculated to characterize bending and hence rigidity.

This second moment of area is expressed in m$^4$ and defined as:

$$I = n \times \pi \times D^4/64$$

where n is the number of filaments of the multifilament thread (n=1 for a monofilament), and D is the diameter of each filament of the multifilament.

The diameter of a thread (or filament) expressed in micrometres (μm) can be determined from the grade of the thread expressed in dtex (corresponding to the linear density P of the thread i.e. mass of the thread in (g) per 10 000 linear metres)
i.e.

$$D = 20 \cdot \sqrt{\frac{P}{(\pi \cdot d)}}$$

where d is the density of the polymer used in the thread e.g. 1.38 for polyester, 1.2 for polyamide and 0.9 for polypropylene, and P is the linear mass of the thread or filament expressed in dtex.

Therefore, for a monofilament of 50 dtex P=50, and for a multifilament of 50/24 dtex the weight of the filament is 50/24 i.e. 2.08.

Using this model, it was possible to calculate the second moment of area for a monofilament and multifilament having the same dtex grade, and the second moments of area for multifilaments as a function of the dtex of the thread and the number of filaments e.g. 50/24 dtex, for a polyester thread for example.

The results are grouped together below and confirm that the second moment of area for a monofilament is higher than that of a multifilament.

Therefore, for the following threads the results are:
Monofilament 22 dtex I=2.10$^{-19}$
Multifilaments 22/12 dtex I=1.7 10$^{-20}$
Monofilament 50 dtex I=1.04 10$^{-18}$
Multifilaments 50/24 dtex I=4.35 10$^{-20}$
Monofilament 55 dtex I=1.26 10$^{-18}$
Multifilaments 55/48 dtex I=2.60 10$^{-20}$
Monofilament 80 dtex I=2.7 10$^{-18}$
Multifilaments 80/70 dtex I=3.82 10$^{-20}$.

It is therefore found that there are major variations in this second moment of area between 2 threads of same dtex value. For example, the second moment of area for a monofilament is in the region of 12 times that of a multifilament for 22 dtex, 24 times for 50 dtex, 48 times for 55 dtex and 70 times for 80 dtex.

It therefore follows from this analysis that the behaviour and characteristics of a 3D multifilament knit will not be the same as those of a monofilament 3D knit.

To promote flexibility and user comfort, the use of multifilament appears to be preferable.

To obtain the most flexible and most comfortable product possible despite narrow thickness to facilitate handling of the bandage, the applicant has therefore examined the behaviour of 3D knit having a multifilament as spacer thread and sought to determine which characteristics said 3D knit should have so that it can be used without the addition of adhesive or latex as compression bandage, and the impact thereof on spiral-over-spiral slippage.

As previously indicated, the chief difference between said multifilament and monofilament threads is that multifilaments have lesser rigidity than a monofilament of equivalent grade.

Their behaviour and impact within a textile structure are therefore neither similar nor predictable compared with a knit having a monofilament as spacer thread.

This is all the more important in a 3D knit in which the multifilament acts as spacer thread both separating and linking the 2 textile surfaces.

The results of the test described below confirmed this difference in behaviour. They showed that with a multifilament as spacer thread the threshold shear stress is not necessarily the sole parameter involved. For example, 3D knits having a threshold shear stress of less than 2800 Pa also allowed preventing of spiral-over-spiral bandage slippage.

Although the physical phenomena involved are highly complex, the present disclosure has found that the ability of the 3D knit—compared with a knit in which the spacer thread is a monofilament—to follow the exact contour of the limb is also an essential parameter which appears either to add to the effect of shear stress or to compensate for the latter if it is too low. This close contact appears to attenuate friction forces on the bandage both in the longitudinal direction and transverse direction during calf movements, and would therefore reduce micromovements along the bandage thereby preventing spiral-over-spiral slippage.

This adaptability of a 3D knit has never been either studied or measured. The flexibility of a textile material cannot be assessed solely from uniaxial tests since any change in its properties in one direction will interfere with the other directions. This phenomenon is all the more complex with 3D knits since the product can vary along three axes x, y and z.

To determine the technical characteristic allowing this property of conforming to the shape and movement of the limb to be obtained, the applicant has adapted technology used in the British Pharmacopeia to measure the deformation of a liquid-impermeable hydrocolloid dressing. The principle is to measure the deformation of an impermeable dressing under pressure induced by compressed air.

The radius of curvature of the dressing is measured when it is subjected to a given pressure.

The present disclosure has adapted this test to 3D knits which are not air-impermeable. This bi-axial deformation test proved to be well adapted for measuring the capability of a 3D knit to adapt to body shape and movement.

It is the measurement of this radius of curvature of the 3D knit that has been termed the conformability of the 3D knit.

By means of the determination of this new test, it was possible to determine all the technical characteristics in terms of threshold shear stress and conformability needed for a 3D knit in which the spacer thread is a multifilament, to ensure prevented spiral-over-spiral slippage of this type of compression bandage.

Once aspect of the present disclosure relates to a bandage having longitudinal elongation of between 30% and 160%, being a 3D knit with a multifilament as spacer thread, obtained using "warp knit" technology, without latex or adhesive, which is non-slip for at least 48 hours and better still for at least 3 days or more. For the treatment of leg ulcers with highly exudative wounds, these minimum periods of 48 and 72 hours correspond to the usual times between change of dressings placed underneath a compression bandage. It is therefore essential that the bandage should remain in place for at least 2 or 3 days without slipping.

Another aspect of the present disclosure relates to a compression bandage in the form of a knit obtained with warp knit technology, formed of synthetic yarns and composed of 2 textile surfaces having the same or different textile structure, linked together by spacer threads which are multifilaments, each textile surface comprising elastic yarns, characterized in that said knit has longitudinal elongation measured as per standard EN 14704-1 of between 30 and 160%, a threshold shear stress equal to or higher than 2800 Pa, and/or conformability equal to or lower than 65 mm.

Tests described below showed that a bandage having at least a threshold shear stress or conformability such as mentioned above can ensure spiral-over-spiral non-slippage of the compression bandage, thereby preventing the intrinsic slackening thereof and maintaining therapeutic efficacy with prevented slippage.

Another aspect of the present disclosure is the 3D knit can be single-use or reusable and therefore washable.

After the knitting operation and to stabilize the 3D knit, in particular to obtain a washable product, its structure is consolidated using frequently employed technologies for this purpose such as heat setting or vaporizing treatment. For these operations, at an additional in-line step with the knitting operation or separate therefrom, the knit is passed through an oven for heat setting or through a flow of water vapour for vaporization at a given rate and at a set temperature.

To promote accurate application by healthcare staff, the compression bandage can be provided with calibration means. These calibration means can be visual e.g. a set of pictograms regularly spaced apart and printed on the bandage or obtained via a calibration system. Information on recommended stretch for application can be provided with the calibration means. Calibration can also be prepared by healthcare staff in the form of a stencil. This type of stencil or the explanations needed to prepare one can be incorporated in the packaging of the bandage. A kit can be used comprising several bandages of different structure, different widths, different lengths and/or provided with different calibrations to apply specific pressures.

The kit may also comprise one or more dressings intended to be placed over the wound before applying the bandage.

To promote ease of handling for application, a knit will be selected having longitudinal elongation such as defined in standard EN 14704-1 of between 40 and 160%, or more specifically between 50 and 120%, or further specifically between entre 55 and 100%.

For example, the knit has a thickness of between 1 and 2 mm, or more specifically between 1 and 1.5 mm.

For example, the knit has a gram weight of 160 to 370 $g/m^2$, or more specifically 180 to 300 $g/m^2$, or further specifically 200 to 250 $g/m^2$.

Similarly, the knit preferably has a spacing between the 2 textile surfaces of between 0.4 and 1.5 mm, or more specifically between 0.5 and 1.1 mm.

These properties of low gram weight and narrow thickness ensure facilitated use of the compression bandage in footwear. The compression bandage can therefore also be used more easily with wadding if necessary.

The two textile surfaces of the knit can have the same or different textile structures. These textile structures can be solid or openwork.

Openwork textile structures called openwork knit and designated herein as net are well known to skilled persons. An openwork knit is a knit having regular or irregular holes in its textile structure. These holes are obtained when one or more stitches in a column, within a textile structure, are not linked to the stitches of the neighbouring column when knitted, typically by acting on the stitch pattern and/or threading.

In accordance with another aspect of the present disclosure, the knit has two textile surfaces having a different textile structure, and in particular one textile surface having an openwork textile structure called net surface and one textile surface having a solid textile surface. The presence of a net surface promotes the breathability of the bandage. The net surface is typically placed in contact with the user's skin.

In accordance with another embodiment of the present disclosure, the knit has one surface having a textile structure of locknit, cord, open or closed loop single tricot, atlas under one or more rows, or open or closed loop pillar stitch type, or alternating closed and open loops. This surface lies opposite the surface adapted to be placed in contact with the skin which is a net having the same or different type of openwork textile structure.

To facilitate passing over the heel and to avoid necking of the bandage at the time of application, 3D knits can be used having transverse elongation greater than 120% as measured in accordance with method A § 9.1 of standard EN 14704-1, or between 120% and 300% for example, or between 120% and 250%.

The knits of the present disclosure are produced for example using yarns routinely employed in the manufacture of textile products and of knits in particular. For example, these yarns are synthetic. They can be divided into two major categories of elastic yarn and thermoplastic yarn.

Among elastic yarns, mention can be made for example of polyurethane fibre yarn such as Elastane yarn marketed under the trade name LYCRA, elastodiene-containing yarns or triblock polymer yarns (styrene—ethylene—butylene—styrene).

Among thermoplastic yarns, mention can be made of yarns of synthetic material which are not elastomers such as polyester, polyamide, polypropylene, polybutylene terephthalate (PBT).

All these thermoplastic yarns can be gimped or non-gimped, texturized or non-texturized.

The two textile surfaces of the 3D knit are formed for example from elastic yarns and thermoplastic yarns. These yarns can be monofilament or multifilament. These textile surfaces can be produced from same or different yarns. Preferably both surfaces comprise similar elastic yarns. The elastic yarns on these textile surfaces have grades in the region of 40 to 80 dtex for example, and the thermoplastic yarns have grades of 40 to 90 dtex.

If it is desired to promote outward transfer of moisture from the knit, it is possible to use yarn of non-synthetic type, such as cotton or viscose, on one of the two surfaces and in particular on the surface in contact with the skin.

Elastane can be used for example as elastic yarn, and polyamide or polyester as thermoplastic yarn.

The spacer threads are typically multifilament thermoplastic threads e.g. polyester, polypropylene or polyamide threads.

By multifilament it is meant thread formed of the association of several continuous filaments linked together by twisting, intermingling, gimping or glue points for example. These threads are defined by the dtex value and the number of constituent filaments e.g. 50/24 dtex which means a yarn of 50 dtex formed of 24 filaments.

In general, these threads are more fragile than monofilament threads, the more so the smaller the diameter of the filaments. For example, threads having a low dtex value are more difficult to knit. Conversely, the higher the number of filaments compared with a monofilament for one same dtex, the thicker the thread which once again is difficult to knit.

In the present disclosure, multifilament threads are preferably chosen of between 20 and 85 dtex wherein the filament is not a microfibre i.e. it has a dtex grade of 1 or higher.

More particular preference is given to multifilaments having a grade of between 20 and 80 dtex, or between 33 and 80 dtex, or between 40 and 80 dtex, or between 40 and 70 dtex, with a number of filaments higher than 12, or more specifically a multifilament in polyester having a dtex grade of between 44 and 55 dtex and a number of filaments of between 12 and 24.

To produce the 3D knit, it is possible for example to use a single bar to knit the spacer thread which links together the 2 textile surfaces.

The present disclosure also concerns a kit having one or more compression bandages such as previously defined, and one or more dressings adapted to be placed over a wound prior to one of the compression bandages.

Still other aspects of the present disclosure will become apparent upon a reading and understanding of the following detailed description.

BRIEF DESCRIPTION OF THE DRAWINGS

The present disclosure is illustrated by the following examples and comparative tests, and in FIGS. 1 to 5.

DETAILED DESCRIPTION OF THE DISCLOSURE

Example of Embodiment of the Invention

A knit of the invention was produced measuring about 10 cm in width on a 22 gauge, double-bed Raschel warp knit loom.

This knit has one surface which comes into contact with the skin which is a net surface, and the opposite-facing surface has a solid surface.

Figure 1:
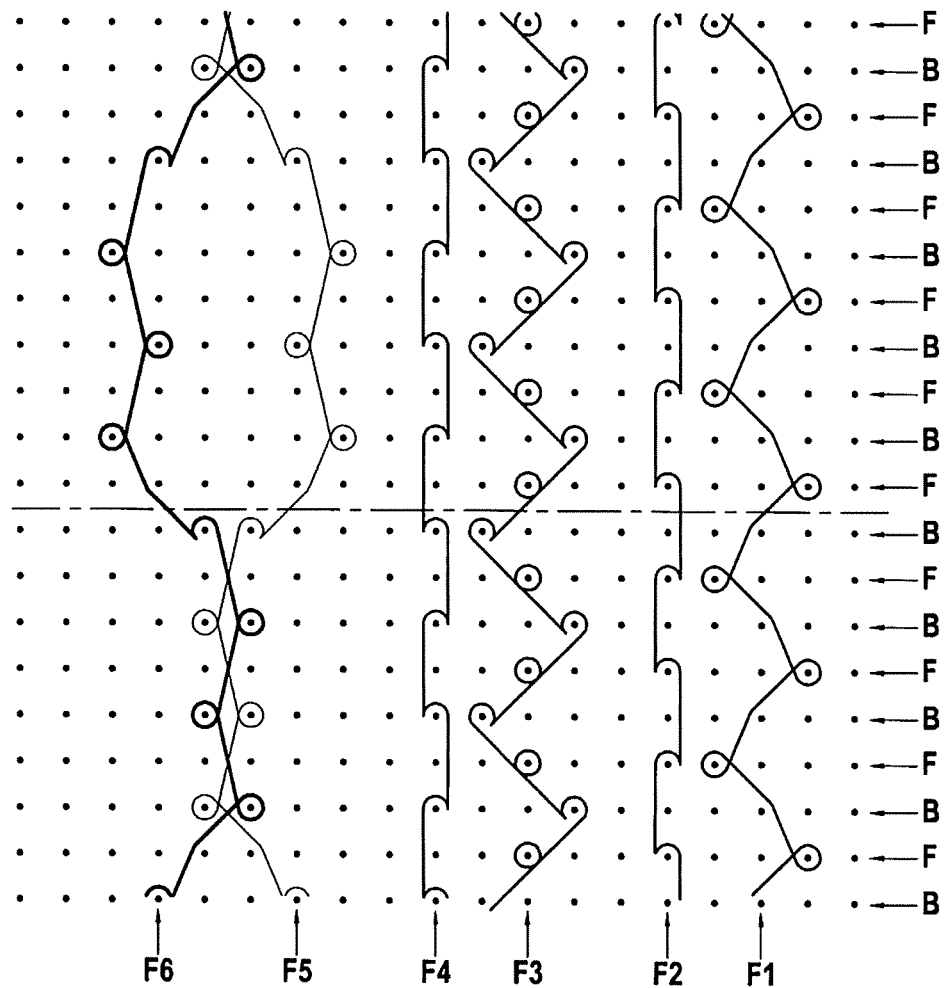
FIG. 1 is a graph of a stitch structure to obtain a knit in accordance with one embodiment of the disclosure.

To produce the knit, 6 bars were used in accordance with the stitch pattern illustrated in FIG. 1 using the following yarns and conditions:

Type of Yarns
    F1: polyamide yarn marketed by RADICI under reference 78/18/1 dtex S Beige
    F2: 44 dtex elastane yarn marketed by ASAHI KASEI GROUP
    F3: multifilament polyester yarn of 50/24 dtex marketed by SINTERAMA
    F4: 44 dtex elastane yarn marketed by ASAHI KASEI GROUP
    F5: polyamide 66 yarn marketed by EMILE TARDY under reference PA 66 1/44/34/FT BE MM
    F6: polyamide 66 yarn marketed by EMILE TARDY under the reference PA 66 1/44/34/FT BE MM Knitting Loom Set-Up
    F1: thread feed of 2400 mm consumed to obtain 480 stitches, full-set threading
    F2: thread feed of 1300 mm consumed to obtain 480 stitches, 1 in/1 miss threading
    F3: thread feed of 3600 mm consumed to obtain 480 stitches, full-set threading F4: thread feed of 2000 mm consumed to obtain 480 stitches, 1 in/1 miss threading
    F5: thread feed of 2100 mm consumed to obtain 480 stitches, 3 in/1 miss threading
    F6: thread feed of 2100 mm consumed to obtain 480 stitches, 3 in/1 miss threading Stitch Pattern FIG. 1 gives the graph of an example of stitch structure to obtain a knit according to one particular embodiment of the present disclosure.

In this Figure the front needle-bed is shown under reference F and the back needle-bed under reference B. The stitch patterns of threads F1 to F6 are then illustrated.

It will be well understood that this example and the following examples are given by way of illustration only and are not to be construed as limiting with regard to the scope of the present disclosure.

The knit thus obtained undergoes an in-line heat setting step.

At this step, the knit was passed in a single pass between 2 rolls formed of heating cylinders so that each surface underwent this treatment at a rate of 5.5 metres per minute. The temperature of the rolls before passing the knit was adjusted to be in the region of 165° C.

The following techniques were used to evaluate the parameters of the knit obtained.

Measurement of Gram Weight

Measurement of gram weight was conducted in accordance with standard NF EN 12127. 5 test specimens were weighed having a surface area of 100 cm² (measurement=±1%) with a balance having accuracy to within 1 mg.

Weighing was performed at a temperature of 21° C.±2° C., and at 60%±15% RH.

The final measurement was a mean of the 5 test specimens.

Measurement of Thickness

Measurement of thickness was performed in accordance with standard NF EN ISO 9073-2. A KEYENCE laser micrometer was used (equipped with CCD LK-G87 laser sensor head and CCD LK-G3001PV laser movement sensor). The application pressure was set at 0.5 kPa and the surface area of the steel disc was 2500 mm².

Measurement of Spacing Between the Surfaces

This measurement was conducted as follows.

Using a KEYENCE digital microscope (lenses×100 or ×200) the spacing was determined between the two planes of the 2 textile surfaces.

The mean plane of the 2 surfaces was evidenced by a horizontal line estimated by the operator, and the distance between the two lines was automatically determined by the software. The measurement was reproduced several times to increase accuracy and a mean of the measurements obtained was calculated.

Measurement of Threshold Shear Stress

Measurements were performed using a DHR2 rheometer marketed by TA Instruments.

They were performed at a temperature of 35° C. (to best approach the temperature of the bandages in contact with the skin), said temperature being adjusted by a Peltier plate equipping the rheometer. 2 discs of 25 mm in diameter were cut from the 3D knit to be analysed. These 2 discs were respectively glued onto the metal surface of the mobile plate and Peltier plate of the rheometer using a thin, rigid, double-sided adhesive marketed by Plasto under reference P753. The 2 discs of the 3D knit were placed in contact, locknit surface structure (also called cord-tricot structure) on net structure, by applying a pressure of 5.3 kPa (i.e. the equivalent of 40 mm of mercury). The piloting programme of the rheometer generates a stress ramp (torsion torque) which varies from 100 to 10 000 Pa in 600 seconds. The apparatus records the first micromovement detected which corresponds to the threshold shear stress expressed in Pa.

It is considered that instrument uncertainty for this measurement is more or less 6%.

The final measurement was the mean of the values obtained for 5 samples of the same 3D knit.

Measurement of Conformability

Figure 4:
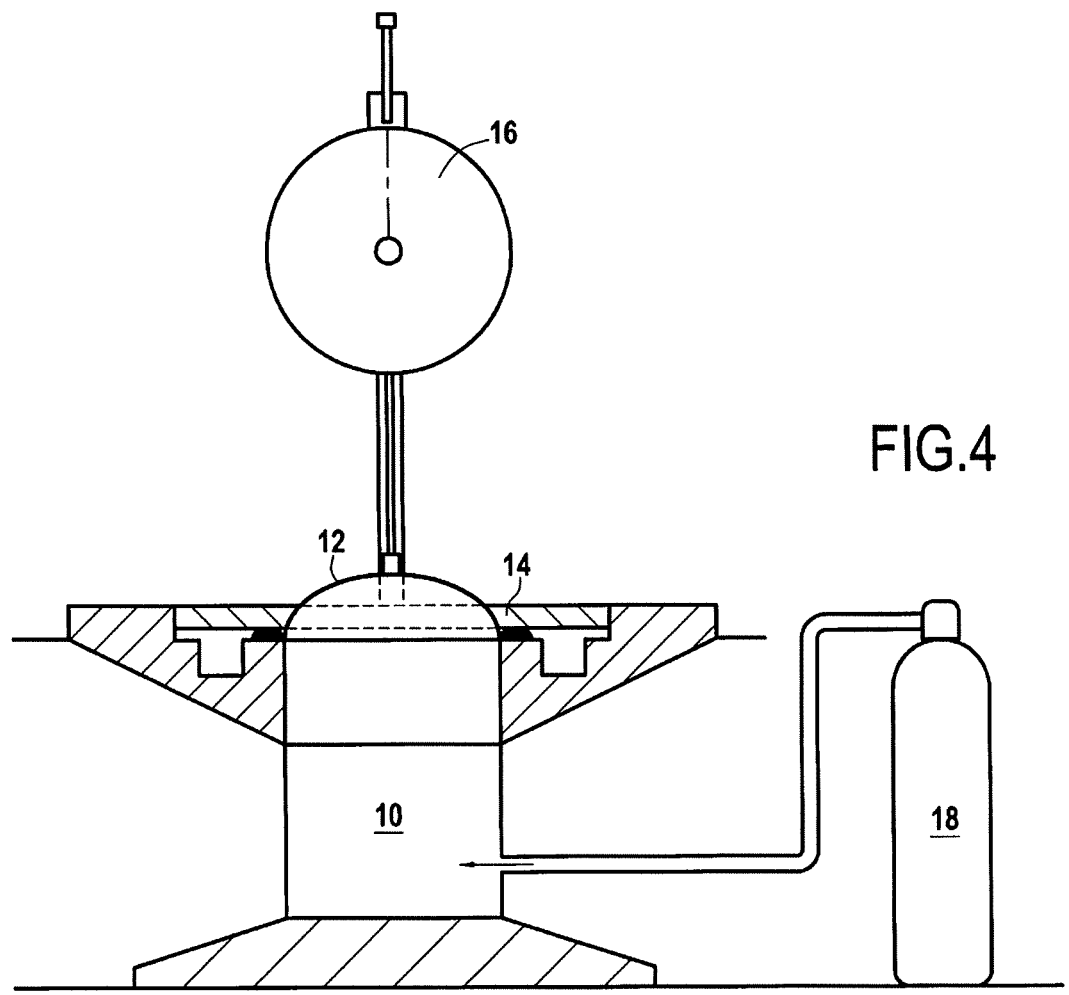
FIG. 4 is a side elevational view showing an apparatus for performing a measurement of conformity in accordance with an embodiment of the present disclosure.
Figure 5:
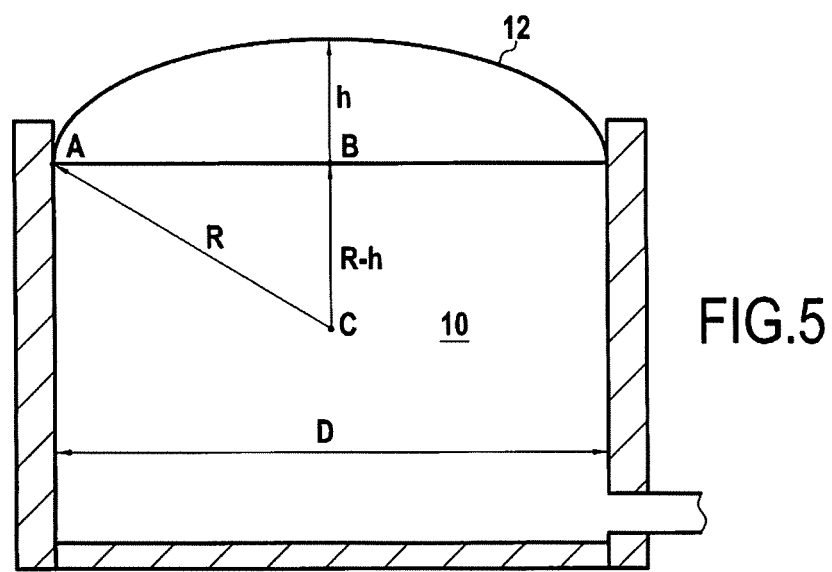
FIG. 5 is a side elevated view of a load cell used for calculating deformation in accordance with an embodiment of the disclosure.

The description of this test is illustrated in FIGS. 4 and 5.

As indicated in FIG. 4, a cell is used to measure deformation which is a cylinder 75 mm in diameter fed with compressed air at a pressure of 50 mbar.

The 3D knits to be tested were left in a conditioned chamber for at least 24 hours at 21° C.±2° C., and 60%±15% relative humidity. A sample 12 of 3D knit was cut using a cutter 99 mm in diameter. Since the 3D knit is permeable to air, a very thin polyurethane film of 30 micrometres was cut to the same diameter. This film provides air-tightness needed to conduct measurement. It has an extensive level of deformation compared with the 3D knit and its presence does not modify the results obtained. In addition, all the knits were comparatively tested in the presence of this film.

The polyurethane film covered by the 3D knit was placed on the measuring cell (10) and clamping was obtained with a pressure device 14 along a sealing plane to make the system airtight.

A micrometre 16 was used to adjust the surface of the sample 12 at 0 mm. The airflow rate was adjusted (provided by a compressed air feed source 18) and the sample 12 left to stabilise for at least one minute. The knit deforms and forms a spherical dome of which the height h is measured with the micrometre 16.

This deformation is expressed by calculating the radius of curvature formed by the 3D knit under the pressure of the compressed air.

The calculation is based on this height h and the diameter D of the measuring cell as illustrated in FIG. 5.

$$R = h/2 + D^2/8h.$$

This radius of curvature R (termed conformability) is expressed in mm. This measurement was reproduced on 7 samples of the same 3D knit and the final value was the mean of these 7 measurements.

The parameters of the knit obtained were the following (Example 1):

Gram weight 234 g/m²

Thickness: 1.39 mm

Threshold shear stress: 2227 Pa

Conformability: 63.6 mm

Spacing between surfaces: 0.9 mm

Longitudinal elongation as per standard EN 14704-1:73%

Transverse elongation as per standard EN 14704-1:144%

Several other knit examples were also produced that are detailed below.

These other examples were produced using the same stitch pattern as detailed for Example 1 (unless otherwise stated). The type of yarns, set-up of the knitting loom and characteristics obtained are given below.

Example 2: Corresponding for Example to a Product which, as in Example 1, has One Surface which Comes into Contact with the Skin which is a Net Surface and the Opposite-Facing Surface is a Solid Surface Having Long Stretch A strip of the product obtained in Example 1 was subjected to 5 successive washings, without drying between each wash, in a washing machine at 40° C. and 800 rpm, with washing product marketed under the trade name "Le Chat machine".

Characteristics of the Product Obtained: (Example 2)

Gram weight: 315/m²

Thickness: 1.6 mm

Threshold shear stress: 3667 Pa

Conformability: 70.3 mm

Spacing between the surfaces: 1.17 mm

Longitudinal elongation as per standard EN 14704-1: 112%

Transverse elongation as per standard EN 14704-1:125%

Figure 2:
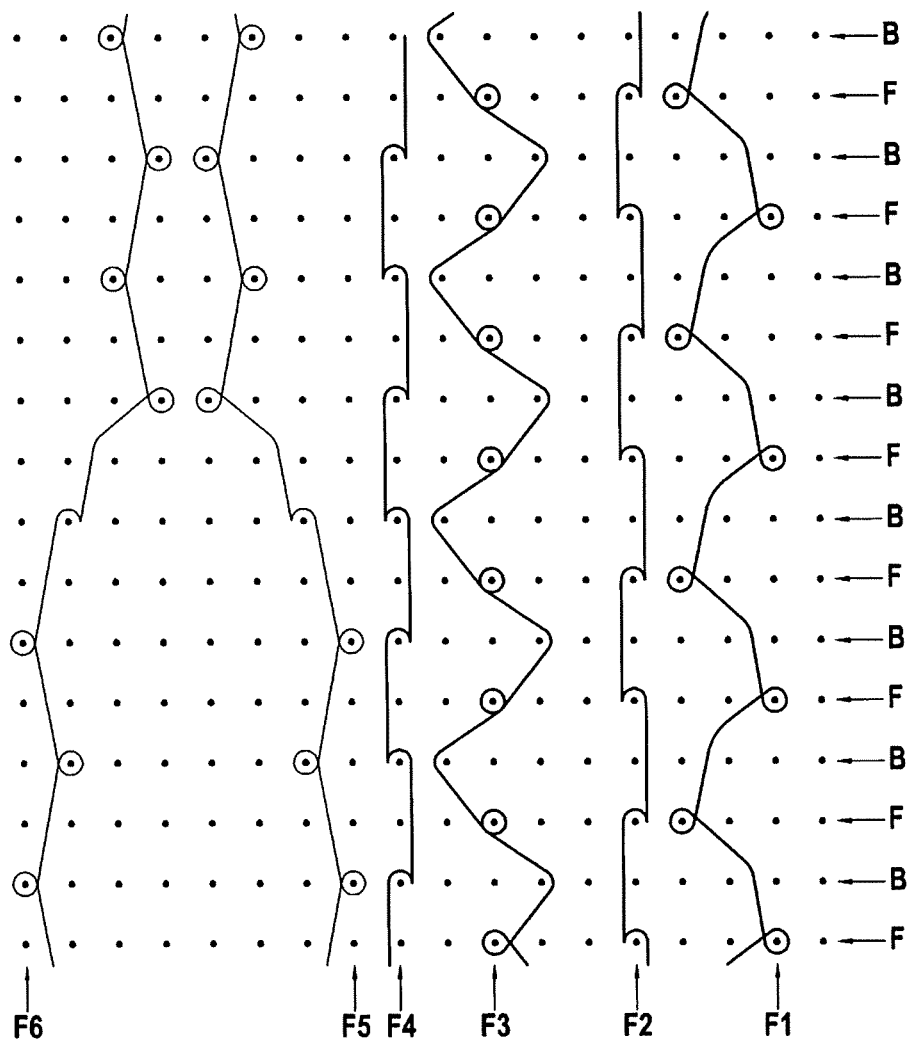
FIG. 2 is a graph of a stitch structure to obtain a knit in accordance with another embodiment of the disclosure.

Example 3: Corresponding for Example to a Product without an Openwork Surface i.e. Having Two Solid Surfaces Type of Yarns:
F1: polyamide yarn marketed by RADICI under reference 78/18/1 dtex S Beige
F2: 44 dtex elastane yarn marketed by ASAHI KASEI GROUP
F3: multifilament polyester yarn of 50/24 dtex marketed by SINTERAMAFILVA
F4: 44 dtex elastane yarn marketed by ASAHI KASEI GROUP
F5: polyamide 66 yarn marketed by Defiber under reference PA 66 1/44/34/dTex
F6: polyamide 66 yarn marketed by Defiber under reference PA 66 1/44/34/dTex The stitch pattern here differs from that of the other examples and is illustrated in FIG. 2.

Knitting Loom Set-Up:
F1: thread feed of 2700 mm consumed to obtain 480 stitches, full-set threading
F2: thread feed of 1300 mm consumed to obtain 480 stitches, 1 in/1 miss threading
F3: thread feed of 3600 mm consumed to obtain 480 stitches, full-set threading
F4: thread feed of 1700 mm consumed to obtain 480 stitches, 1 in/1 miss threading
F5: thread feed of 2000 mm of consumed to obtain 480 stitches, 3 in/1 miss threading
F6: thread feeding of 2000 mm consumed to obtain 480 stitches, 3 in/1 miss threading The knit thus obtained was then subjected to a step for in-line heat setting.

At this step, the knit was passed in a single pass between 2 rolls formed of heating cylinders so that each surface underwent this treatment at a rate of 5 metres per minute. The temperature of the rolls before passing the knit was adjusted to be in the region of 165° C.

Characteristics of the Product Obtained: (Example 3)
Gram weight: 264/m$^2$
Thickness: 1.5 mm
Threshold shear stress: 2217 Pa
Conformability: 63.3 mm
Spacing between surfaces: 1.21 mm
Longitudinal elongation as per standard EN 14704-1: 89%
Transverse elongation as per standard EN 14704-1: 176%

Example 4: Corresponding for Example to a Product without an Openwork Surface i.e. Having 2 Solid Surfaces Type of Yarns:
F1: polyamide yarn marketed by RADICI under reference 78/18/1 dtex S Beige
F2: 44 dtex elastane yarn marketed by ASAHI KASEI GROUP
F3: 50/24 dtex polyester multifilament yarn marketed by SINTERAMAFILVA
F4: 44 dtex elastane yarn marketed by ASAHI KASEI GROUP
F5: polyamide 66 yarn marketed by Defiber under reference PA 66 1/44/34/dTex
F6: polyamide 66 yarn marketed by Defiber under reference PA 66 1/44/34/dTex The stitch pattern here was identical to the one in Example 3 and is illustrated in FIG. 2.

Knitting Loom Set-Up:
F1: thread feed of 2700 mm consumed to obtain 480 stitches, full-set threading
F2: thread feed of 1300 mm to obtain 480 stitches, 1 in/1 miss threading
F3: thread feed of 3600 mm consumed to obtain 480 stitches, full-set threading F4: thread feed of 1700 mm consumed to obtain 480 stitches, 1 in/1 miss threading
F5: thread feed of 2000 mm consumed to obtain 480 stitches, 3 in/1 miss threading
F6: thread feed 2000 mm consumed to obtain 480 stitches, 3 in/1 miss threading.

The knit obtained was subjected to a step for in-line heat setting.

At this step, the knit was passed in a single pass between 2 rolls formed of heating cylinders so that each surface underwent this treatment at a rate of 3.75 metres per minute. The temperature of the cylinders before passing the knit was adjusted to be in the region of 165° C.

Characteristics of the Product Obtained: (Example 4)
Gram weight: 267/m$^2$
Thickness: 1.6 mm
Threshold shear stress: 2207 Pa
Conformability: 67.1 mm
Spacing between surfaces: 1.46 mm
Longitudinal elongation as per standard EN 14704-1: 93%
Transverse stretching as per standard EN 14704-1: 174%

Figure 3:
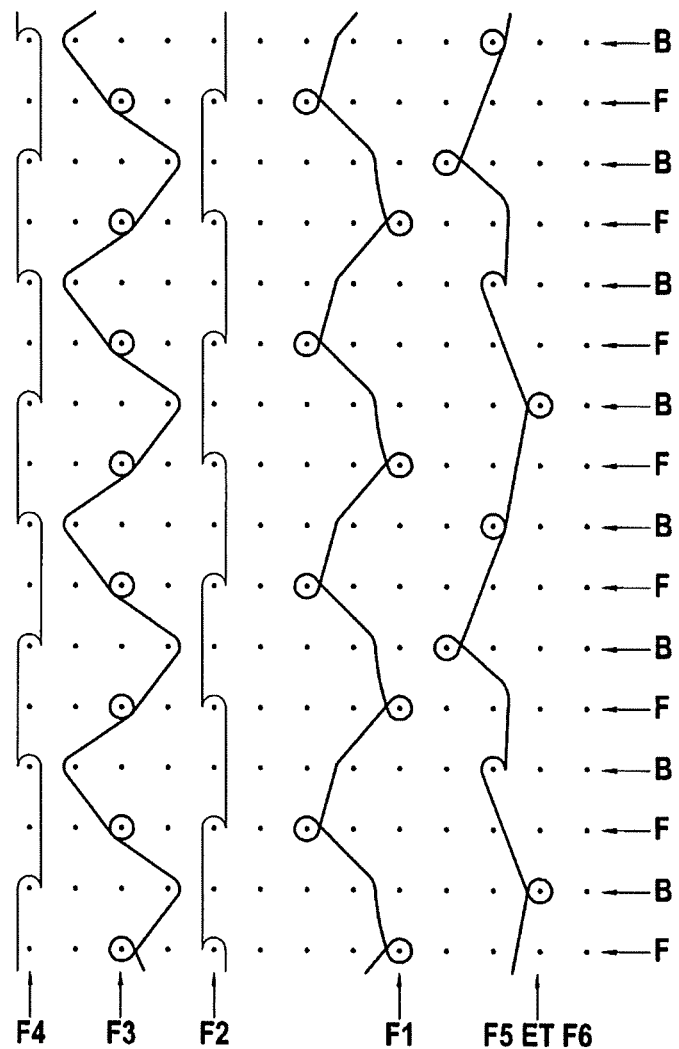
FIG. 3 is a graph of a stitch structure to obtain a knit in accordance with another embodiment of the disclosure.

Example 5: Corresponding for Example to a Product Having a Net Surface in Contact with the Skin and the Opposite-Facing Surface being a Solid Surface Type of Yarns:
F1: polyamide yarn marketed by RADICI under reference 78/18/1 dtex S Beige
F2: 44 dtex elastane yarn marketed by ASAHI KASEI GROUP
F3: multifilament polyester yarn of 50/24 dtex marketed by SINTERAMAFILVA
F4: 44 dtex elastane yarn marketed by ASAHI KASEI GROUP
F5: polyamide 66 yarn marketed by Defiber under reference PA 66 1/44/34/dTex
F6: polyamide 66 yarn marketed by Defiber under reference PA 66 1/44/34/dTex The stitch pattern here differed from the other examples and is illustrated in FIG. 3.

Knitting Loom Set-Up:
F1: thread feed of 2700 mm consumed to obtain 480 stitches, full-set threading
F2: thread feed of 1300 mm to obtain 480 stitches, 1 in/1 miss threading
F3: thread feed of 4000 mm consumed to obtain 480 stitches, full-set threading
F4: thread feed of 1700 mm consumed to obtain 480 stitches, 1 in/1 miss threading
F5: thread feed of 2000 mm consumed to obtain 480 stitches, 3 in/1 miss threading
F6: thread feed of 2000 mm consumed to obtain 480 stitches, 3 in/1 miss threading The knit thus obtained was subjected to a step for in-line heat setting.

At this step, the knit was passed in a single pass between 2 rolls formed of heating cylinders so that each surface underwent this treatment at a rate of 5.5 metres per minute.

The temperature of the cylinders before passing the knit was adjusted to lie in the region of 165° C.
Characteristics of the Product Obtained: (Example 5)
  Gram weight: 274/m²
  Thickness: 1.7 mm
  Threshold shear stress: 1707 Pa
  Conformability: 67.4 mm
  Spacing between surfaces: 1.32 mm
  Longitudinal elongation as per standard EN 14704-1:88%
  Transverse elongation as per standard EN 14704-1:168%

Example 6: Corresponding to a Knit with a Monofilament

A knit was produced about 10 cm in width according to the invention on a gauge 22, double-bed warp knit Raschel loom.

This knit has a net surface in contact with the skin and opposite-facing solid surface.

Type of Yarns
  F1: polyamide yarn marketed by RADICI under reference 78/18/1 dtex S Beige
  F2: 44 dtex elastane yarn marketed by ASAHI KASEI GROUP
  F3: monofilament polyester 55 dtex yarn marketed by FILVA
  F4: 44 dtex elastane yarn marketed by ASAHI KASEI GROUP
  F5: polyamide 66 yarn marketed by EMILE TARDY under reference PA 66 1/44/34/FT BE MM
  F6: polyamide 66 yarn marketed by EMILE TARDY under reference PA 66 1/44/34/FT BE MM Knitting Loom Set-Up
  F1: thread feed of 2500 mm consumed to obtain 480 stitches, full-set threading
  F2: thread feed of 1500 mm consumed to obtain 480 stitches, 1 in/1 miss threading
  F3: thread feed of 3500 mm consumed to obtain 480 stitches, full-set threading
  F4: thread feed of 1600 mm consumed to obtain 480 stitches, 1 In/1 miss threading
  F5: thread feed of 2250 mm consumed to obtain 480 stitches, 3 in/1 miss threading Stitch Pattern The stitch pattern here was the same as in Example 1 and is therefore illustrated in FIG. 1.

The knit thus obtained was subjected to a step for in-line heat setting.

At this step, the knit was passed in a single pass between 2 rolls formed of heating cylinders so that each surface underwent this treatment at a rate of 5.5 metres per minute. The temperature of the rolls before passing the knit was adjusted to lie in the region of 190° C.

Characteristics of the product obtained: (Example 6)
  Gram weight 232 g/m²
  Thickness: 1.23 mm
  Threshold shear stress: 3080 Pa
  Conformability: 66.2 mm
  Spacing between surfaces: 0.64 mm
  Longitudinal elongation as per standard EN 14704-1:56%
  Transverse elongation as per standard EN 14704-1:128%

Next, a test described below was performed to compare the in vitro pressure performance between Examples 3 and 6 of the present disclosure and the two-layer compression system marketed under the trade name K2 by URGO.

In Vitro Test

The performance of the 3D knit in Examples 3 and 6 and of the two-layer compression system marketed under the tradename K2 by URGO were evaluated in terms of working pressure and resting pressure and the pressure difference over time.

The in vitro test method and apparatus described in patent application WO 2007/113430 was used, page 17 line 26 to page 19 line 18. According to this method, the bandage was applied around a roll with 100% coverage and the circumference of the roll was caused to vary at a rate continually imposed between a so-called resting position (smallest diameter) and so-called working position (largest diameter) to imitate muscle contraction.

Pressure sensors measured the values over time of the resting and working pressures.

The time interval between measurements of working pressure and resting pressure was 5 seconds and the frequency of measurement of these two successive parameters was 0.2 Hz.

To test the compression bandages of the invention, the longitudinal stretch of the bandage on application was determined as a function of the desired working pressure e.g. using the elongation at rupture curve such as defined in standard EN ISO 13934-1. According to Laplace's law, the elongation to be applied corresponds to the desired pressure.

A rectangular strip is cut of sufficient width, fraying if necessary to obtain a sample having a final width of 50 mm. This sample is placed in the jaws of a dynamometer distanced apart by 200 mm. The tensile test is carried out until rupture of the sample at a rate of 100 mm/mn. The test is repeated for 5 samples. Conditioning, hygrometry and temperature conditions are defined in standard EN ISO 13934-1.

Elongation on application was therefore determined at 40% for the bandage according to Example 6 and 70% for the bandage in Example 3 of the present disclosure, to obtain a maximum pressure on application of approximately 50 to 70 mm of mercury.

For accurate application of the bandage, the bandages were calibrated with a pressure indicator as described in patent application WO 2007/113340 page 13, line 18 to page 14, line 6.

The results obtained for the bandage obtained in the examples of the invention and for the two-layer compression system marketed by URGO under the trade name K2 size 18-25 cm are grouped together in Table 1 below.

The value «Max Pressure at T0» corresponds to the first working pressure recorded immediately after application, and "Delta at T" corresponds to the pressure difference between the first working pressure and the first resting pressure recorded immediately after application. The values "Max Pressure at T24" and "Delta at T24" correspond to the measurements recorded 24 hours after application measured in mm of mercury. The difference was the calculated between T0 and T24 hours "Delta (T0–T24 h)".

TABLE 1

| Example 6 | Example 3 | K2 (URGO) | Measurement taken |
|---|---|---|---|
| 40% | 70% | 55% + 50% | Elongation on application |
| 69 | 61 | 44 | Max. pressure at T0 |
| 28 | 26 | 19 | Delta at T0 |
| 51 | 38 | 35 | Max. pressure at T24 |

TABLE 1-continued

| Example 6 | Example 3 | K2 (URGO) | Measurement taken |
|---|---|---|---|
| 25 | 23 | 17 | Delta at T24 |
| +3 | +3 | +2 | Delta (T0 – T24) |

This Table shows that the results obtained in terms of pressures applied at 24 hours and pressure difference at 24 hours, both for the K2 two-layer system and the single bandages of the invention, lie within the targeted ranges namely a maximum pressure at 24 hours of between 35 and 50 mm of mercury and pressure difference at 24 hours of between 15 and 25 mm of mercury. The values of the pressure differences at 24 hours, which are important for treatment efficacy, are even higher for the single bandages of the invention namely 23 to 25 mm of mercury compared with 17 mm of mercury for the K2 two-layer system. It is also ascertained that for the products of Examples 3 and 6 and the K2 product, which are all short-stretch, this pressure difference varies little over time since the variation is +3 for the knits of the present disclosure and +2 for the K2 two-layer system.

Similar results were obtained whether the spacer thread was mono- or multifilament.

To conclude, the bandages of the invention allow equivalent therapeutic properties to those of the K2 product to be obtained, even higher, and allow these properties to be maintained over time with a single bandage and without latex or adhesive.

Similarly, an in vivo test described below was carried out for comparison of Examples 1 to 6 and the K2 product, to evaluate intrinsic slackening of the bandages over time.

The operating mode for this in vivo test was as follows.

The bandages were wound around the leg following the recommendations given in the package leaflet for the K2 two-layer system.

It is recalled that this leaflet recommends the following application method:
1) Place foot at 90° angle, "toes to nose". Apply KTECH from the base of the toes with 1 or 2 turns to anchor in place, ensuring the wadding is in contact with the skin and the pressure indicator is at the top edge, towards the patient. Secure the heel with a figure of eight, ensuring full coverage of the heel without applying full stretch when bandaging the foot.
2) Apply in a spiral up the leg to the knee stretching the bandage appropriately: the pressure indicator printed on the bandages must form a circle. To obtain proper overlap, the pressure indicator must be just covered (50% overlap). Finish 2 cm below the knee and cut off any excess bandage. Secure with tape.
3) Apply KPRESS over KTECH using the same technique starting one finger width above KTECH and finishing one finger width below KTECH so that only KTECH is in direct contact with the skin. Once applied, press gently on the bandage with hands to ensure good cohesion of the system. It will be understood that this latter step 3) is not necessary for a compression bandage of the present disclosure.

For the examples of the present disclosure, as previously for the in vitro test, elongation on application was determined to obtain a maximum pressure at T=0 of between 50 and 70 mm of mercury and the knits were accordingly calibrated in similar manner.

The bandages were wound around the foot, heel and along the leg as far as the knee with 50% overlap. The last spiral was self-secured with a metal clip, tape or preferably with 2 hooked male parts of a Velcro strip. If it is desired to check the pressure applied by the bandage, it is possible at a point B1, corresponding to the area where the Achilles tendon becomes calf muscle i.e. generally about 10 to 15 cm above the malleolus, to place an interface pressure sensor such as the sensor referenced KKH-01 by KIKUHIME. Using a thin felt marker pen, a vertical line was drawn over at least 3 spirals, on the axis of the tibial spine from the last wound spiral. This mark was used as reference, using a mm-graduated rule, to evaluate the horizontal offset of the line on completion of the test. During movements this line loses its rectilinear shape and appears in scale intervals that have larger offset the greater the slippage of the spirals over each other. If spiral-over-spiral slippage is very small or non-existent the vertical line remains intact or varies very little mainly on the first spiral underneath the last wound spiral.

This offset of the vertical line represents slackening of the bandage and illustrates potential slippage over time.

This test was conducted for 6 hours on the same person. This person wore on one leg a bandage of the Examples accordingly calibrated, measuring 10 cm in width and 2.6 m in length (net surface in contact with the skin if the bandage had a net surface), and on the other leg either the K2 two-layer system or another bandage of the invention.

After 6 hours, the offset of the vertical line was measured on the 4 first spirals.

The results were as follows:

K2 two-layer system: no offset of the line on any spiral.

Said result is coherent on account of the "cohesiveness" of the bandage which blocks slippage of spirals over each other.

Compression bandage according to Examples 1 to 6:

The results obtained for these 6 examples are grouped together in Table 2.

| Example | Stress | Conformability | Spiral 1 | Spiral 2 | Spiral 3 | Spiral 4 | Application |
|---|---|---|---|---|---|---|---|
| 1 | 2227 | 63.6 | 1 | 0 | 0 | 0 | 60% |
| 2 | 3667 | 70.3 | 1 | 0 | 0 | 0 | 85% |
| 3 | 2217 | 63.3 | 1 | 0 | 0 | 0 | 70% |
| 4 | 2207 | 67.1 | 15 | 6 | 4 | 4 | 70% |
| 5 | 1707 | 67.4 | 22 | 7 | 2 | 0 | 65% |
| 6 | 3080 | 66.2 | 4 | 0 | 0 | 0 | 40% |

This Table illustrates the essential characteristics that a 3D knit with multifilament spacer thread should have, namely shear stress equal to or higher than 2800 Pa and/or conformability equal to or lower than 65 mm. For the products of Examples 1, 2 and 3 which have at least one of these characteristics, no offset of the line was observed after 6 hours on spirals 2, 3 and 4, with a slight offset of approximately 1 mm on the first spiral lying underneath the last wound spiral.

This value of 1 mm is negligible. It is considered that a mean value of 4 mm for several persons is not representative and reflects measurement uncertainties related to variation in test calf size, reproducibility of application and variability in bandage manufacture.

This is the result obtained with Example 6 which was tested on 6 different persons, and is a monofilament.

The important presence of at least one of these characteristics for a 3D knit having a multifilament spacer thread is particularly evidenced when comparing the products with each other.

Examples 3 and 4 have very close shear stress values in the region of 2200 but Example 3, which has conformability of 63.3 hence lower than 65, exhibited practically no spiral-over-spiral offset, whereas Example 4 which has conformability of 67.1 hence higher than 65 exhibited offset on the 4 spirals after 6 hours and of 15 mm on the first spiral.

Conformability therefore allows compensation for shear stress that is too low. This result was found for Example 1 in which the stress is 2227 Pa but conformability is 63.6 mm.

Conversely, in Example 2 the stress is higher than 2800 Pa i.e. 3667 Pa and no spiral-over-spiral offset was observed even though conformability was 70.3 mm. Finally, Example 5 which has none of these characteristics showed offset over the 3 first spirals and of 22 mm on the first spiral.

Overall, the same conclusions were reached whether the knit has an openwork surface (Examples 1, 2 and 5) or 2 solid surfaces (Examples 3 and 4).

To conclude, even if the causes are unknown, a 3D knit with multifilament spacer thread has equivalent behaviour to one having a monofilament spacer thread, provided it has a shear stress of 2800 Pa or higher as essential characteristic.

If the shear stress is lower than this value, but conformability is 65 mm or lower, this essential characteristic can compensate for the value of shear stress that is too low.

It can therefore be considered that a bandage of the invention having at least one of these 2 characteristics has resistance to spiral-over-spiral slippage that is equivalent to that of a cohesive system or of a 3D knit having a monofilament as spacer thread.

This test shows that in terms of hold these products are equivalent.

All these in vivo and in vitro tests demonstrate that it has been possible to obtain a compression device with only a single bandage which provides the right therapeutic properties and remains non-slip over time without the inclusion of additional substances.

The exemplary embodiment has been described with reference to the preferred embodiments. Obviously, modifications and alterations will occur to others upon reading and understanding the preceding detailed description. It is intended that the appended claims be construed as including all such modifications and alterations insofar as they come within the scope of the embodiments or the equivalents thereof.

The invention claimed is:

1. A compression bandage formed as a single knit obtained with warp knit technology, consisting of synthetic yarns and composed of two textile surfaces having the same or different textile structure, linked together by spacer threads, each of the two textile surfaces comprising elastic yarns, said knit comprising no adhesive and no latex, wherein said spacer threads of said knit are multifilaments, said knit having:

longitudinal elongation measured as per standard EN 14704-1 of between 30 and 160%;

threshold shear stress in the range of 2800 Pa to 3667 Pa and/or conformability equal to or lower than 65 mm.

2. The compression bandage according to claim 1, wherein the knit has a spacing between the two textile surfaces of between 0.4 and 1.5 mm.

3. The compression bandage according to claim 2, wherein the knit has a spacing between the two textile surfaces of between 0.5 and 1.1 mm.

4. The compression bandage according to claim 3, wherein the knit has a gram weight of between 160 and 300 g/m2.

5. The compression bandage according to claim 1, wherein the spacer thread is a multifilament having a grade of between 20 and 80 dtex.

6. The compression bandage according to claim 5, wherein the spacer thread has a grade of between 40 and 80 dtex.

7. The compression bandage according to claim 1, wherein the knit has a thickness of between 1 and 2 mm.

8. The compression bandage according to claim 7, wherein the knit has a thickness of between 1 and 1.5 mm.

9. The compression bandage according to claim 1, wherein said knit has one surface having a textile structure from among the following list:
   locknit;
   open or closed loop single tricot;
   atlas under one or more rows;
   open or closed loop pillar stitch, or alternating closed and open loops;
   said one surface lying opposite a surface adapted to be placed in contact with skin and having a net textile structure with openwork textile structure.

10. The compression bandage according to claim 1, wherein the knit has a gram weight of between 160 and 370 g/m$^2$.

11. The compression bandage according to claim 1, wherein the knit has longitudinal elongation such as defined in standard EN 14704-1 of between 50 and 120%.

12. The compression bandage according to claim 1, wherein the knit is produced using a single bar for the spacer threads which link together the two textile surfaces.

13. The compression bandage according to claim 1, wherein a grade of the elastic yarns is between 40 and 80 dtex.

14. The compression bandage according to claim 1, wherein the two textile surfaces comprise thermoplastic yarns having grades of 40 to 90 dtex.

15. A kit comprising one or more compression bandages according to claim 1 and one or more dressings adapted to be placed over a wound prior to application of the compression bandage.

* * * * *